US007069926B2

(12) United States Patent
Skellern et al.

(10) Patent No.: US 7,069,926 B2
(45) Date of Patent: Jul. 4, 2006

(54) FLASHLIGHT AND CANISTER INTERCONNECTION SYSTEM AND METHOD

(76) Inventors: Michael J. Skellern, 15 Ronsard, Newport Coast, CA (US) 92657; Dennis Cole, 1571 Summit Ave., Cardiff by the Sea, CA (US) 92007

( * ) Notice: Subject to any disclaimer, the term of this patent is extended or adjusted under 35 U.S.C. 154(b) by 0 days.

(21) Appl. No.: 11/005,125

(22) Filed: Dec. 6, 2004

(65) Prior Publication Data

US 2005/0166914 A1 Aug. 4, 2005

Related U.S. Application Data

(63) Continuation-in-part of application No. 10/851,717, filed on May 21, 2004.

(60) Provisional application No. 60/515,547, filed on Oct. 30, 2003.

(51) Int. Cl.
*A61M 11/00* (2006.01)
*A61M 16/00* (2006.01)
*A61M 15/00* (2006.01)

(52) U.S. Cl. ............................ 128/200.14; 128/200.11; 128/200.12; 128/200.21; 128/200.23; 128/202.16; 128/202.17; 128/203.23; 128/204.22

(58) Field of Classification Search ........... 128/200.14, 128/200.11, 200.12, 200.21, 200.23, 202.16, 128/202.17, 203.23, 204.22
See application file for complete search history.

(56) References Cited

U.S. PATENT DOCUMENTS

| | | | | |
|---|---|---|---|---|
| 2,855,497 | A * | 10/1958 | Bacon | 362/96 |
| 3,638,836 | A * | 2/1972 | Vickers, III | 222/113 |
| 3,716,170 | A * | 2/1973 | Mangels | 222/162 |
| 3,776,429 | A * | 12/1973 | DeLucia | 222/162 |
| RE28,537 | E * | 9/1975 | Vickers, III | 222/192 |
| 4,186,851 | A * | 2/1980 | Cantor | 222/113 |
| 4,223,804 | A * | 9/1980 | Morris et al. | 222/3 |
| 4,427,844 | A * | 1/1984 | Saby et al. | 174/188 |
| 5,086,377 | A * | 2/1992 | Roberts | 362/102 |
| 5,307,249 | A * | 4/1994 | Vanwynsberghe | 362/96 |
| 5,331,523 | A * | 7/1994 | Delzer | 362/96 |
| 5,373,427 | A * | 12/1994 | McLean | 362/96 |
| 5,420,766 | A * | 5/1995 | Hollis | 362/96 |
| 5,446,985 | A * | 9/1995 | Chen | 42/1.08 |
| 5,673,819 | A * | 10/1997 | Brunswig | 222/113 |
| 5,683,168 | A * | 11/1997 | Teig et al. | 362/96 |
| 5,941,629 | A * | 8/1999 | Tuscher | 362/253 |
| 6,736,523 | B1 * | 5/2004 | Alvey | 362/158 |
| 6,764,347 | B1 * | 7/2004 | Plishner | 439/668 |

* cited by examiner

*Primary Examiner*—Henry Bennett
*Assistant Examiner*—Nihir Patel
(74) *Attorney, Agent, or Firm*—Stetina Brunda Garred & Brucker

(57) ABSTRACT

A flashlight for dispensing a substance from an aerosol canister, the flashlight including an elongated housing having a front end, a rear end, and a central longitudinal axis, the aerosol canister being slidably received and fixedly positionable within the housing. At least one light emitting diode disposed approximate the front end of the housing and an elongated spray tube having a proximal end and a distal end, the proximal end being connected to the aerosol canister and the spray tube extending parallel to the central longitudinal axis such that the distal end extends beyond the front end of the housing.

6 Claims, 6 Drawing Sheets

FLASHLIGHT AND CANISTER INTERCONNECTION SYSTEM AND METHOD

CROSS-REFERENCE TO RELATED APPLICATIONS

The present application is a continuation-in-part of U.S. patent application Ser. No. 10/851,717, filed May 21, 2004, entitled SELF-DEFENSE FLASHLIGHT EQUIPPED WITH AN AEROSOL DISPENSER, which claims priority to provisional application Ser. No. 60/515,547, filed Oct. 30, 2003, entitled LASER AND TEAR GAS EQUIPPED SELF-DEFENSE LED FLASHLIGHT, the teachings of which are expressly incorporated herein by reference.

STATEMENT RE: FEDERALLY SPONSORED RESEARCH/DEVELOPMENT

Not Applicable

BACKGROUND OF THE INVENTION

Threats to personal safety cover a broad spectrum of potential injury and/or lethality to individuals, for example, ranging from simple assault to loss of life. Weapons such as pistols, rifles, and other firearms are often useful as self-defense devices, however, the use of these weapons is not always appropriate for self-defense in that the potential for death or serious bodily injury may often far outweigh the potential injury to the user that feels threatened. As such, it is apparent that varying levels of non-lethal force alternatives are needed to respond to varying levels of potential danger.

Law enforcement officers, military personnel, etc., often find it necessary to rely on non-lethal force to properly perform their duties. For example, acts such as dispersing protestors or riotous crowds seldom, if ever, requires a use of lethal force. Unfortunately, existing non-lethal force devices are typically maintained in the patrol car, vehicle, etc., in which the enforcement personnel travel, making them somewhat inaccessible. Moreover, the use of a non-lethal device that is readily available to a law enforcement official could actually prevent the official from having to rely on unholstering and potentially discharging a firearm. Instances of the use of lethal force often lead to loss time on the job for the concerned official and legal costs for his employer due to legal action stemming from the use of force. These issues can potentially be avoided with the use of non-lethal force.

Individuals also have an interest in the use of non-lethal self-defense devices. Although many individuals can gain access to firearms and other potentially lethal devices, they are often not readily available to others. Moreover, as in the case of law enforcement officials, the use of firearms and other lethal devices is not always commensurate with the level of harm the individual faces. Also, some individuals do not feel capable of, or properly trained to, use lethal devices in their defense. Also, some individuals do not believe the use of lethal force is appropriate in that there is the potential for injuring and/or killing innocent individuals, such as family members residing in the same residence.

Therefore, there is a need for improved non-lethal self-defense equipment which addresses these and other shortcomings of the prior art.

BRIEF SUMMARY OF THE INVENTION

Briefly described, the present disclosure relates a flashlight for dispensing a substance from an aerosol canister. The flashlight includes an elongate housing having a front end, a rear end, and a central longitudinal axis, the aerosol canister being slidably received within the housing. Preferably, the aerosol canister and housing within which the canister is received are configured to interconnect with one another such that the aerosol canister is maintained in a stationary, non-rotatable configuration when axially disposed within the housing. The flashlight also includes at least one light emitting diode disposed approximate the front end of the housing and an elongated spray tube having a proximal end and a distal end. The proximal end of the spray tube is connected to the aerosol canister and the spray tube extends parallel to the central longitudinal axis such that the distal end extends beyond the front end of the housing.

A further embodiment of a flashlight for dispensing a substance from an aerosol canister includes an elongate housing having a front end and a rear end, the aerosol canister being slidably received within the housing. In a preferred embodiment, the aerosol canister and housing are configured to interconnect with one another such that the aerosol canister remains in a fixed, axial orientation within such housing. The flashlight also includes a light source disposed adjacent the front end of the housing and a spray tube having a proximal end and a distal end. The proximal end is connected to the aerosol canister and the distal end extends beyond the front end of the housing such that the substance can be discharged therefrom in a desired direction. A laser diode disposed approximate the front end of the housing is arranged to emit a laser in the desired direction of discharge.

Yet another embodiment of a flashlight for dispensing a substance from an aerosol canister includes an elongate housing having a front end and a rear end, the aerosol canister being slidably received within the housing. As per the other aforementioned embodiments, the aerosol canister is preferably configured to interlock and interconnect with the elongate housing such that the aerosol canister is retained in a fixed, non-rotatable configuration when disposed within the housing. The flashlight also includes a light source disposed approximate the front end of the housing and a spray tube having a proximal end and a distal end. The proximal end is in fluid communication with the aerosol canister and the distal end extends beyond the front end of the housing. The flashlight further includes a switch assembly including a plunger extending into the housing, the plunger being configured to cause the substance in the aerosol canister to be emitted through the spray tube when the plunger is urged inwardly. A switch door is operable between an open and a closed position such that moving the switch door from the closed position to the open position allows a user to access the plunger.

Other objects, features and advantages of the present disclosure will become apparent upon reading the following specification, taken in conjunction with the accompanying drawings.

BRIEF DESCRIPTION OF THE DRAWINGS

Many aspects of the self-defense flashlight can be better understood with reference to the following drawings. The components in the drawings are not necessarily to scale, emphasis instead being placed upon clearly illustrating the principles of the self-defense flashlight. Moreover, in the drawings, like reference numerals designate corresponding parts through the several views.

DETAILED DESCRIPTION OF THE INVENTION

Figure 1:
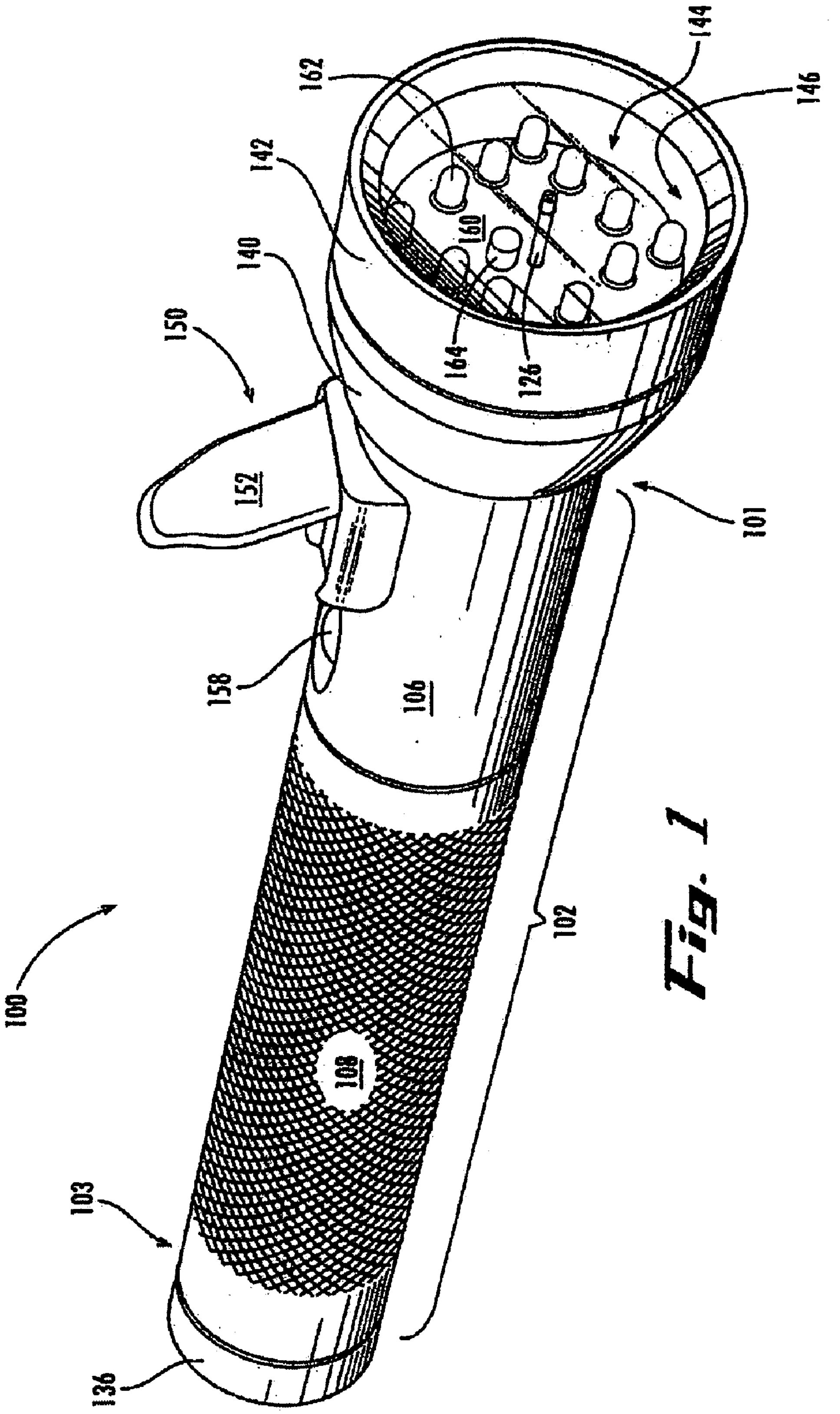
FIG. 1 is a perspective view of a self-defense flashlight constructed in accordance with an embodiment of the present disclosure.

Reference will now be made in detail to the description of the self-defense flashlight as illustrated in the drawings. While the self-defense flashlight will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

In particular, FIG. 1 illustrates a non-lethal self-defense device, in the form of a flashlight 100. In its assembled state, visible components of the preferred embodiment of the flashlight 100 shown include an elongated housing 102 including a front housing 106 and a rear housing 108, a switch assembly 150 also located on the housing 102, a rear cap 136, located at the rear end 103 of the housing 102, and a head 140 located on the front end 101 of the housing 102.

Figure 2:
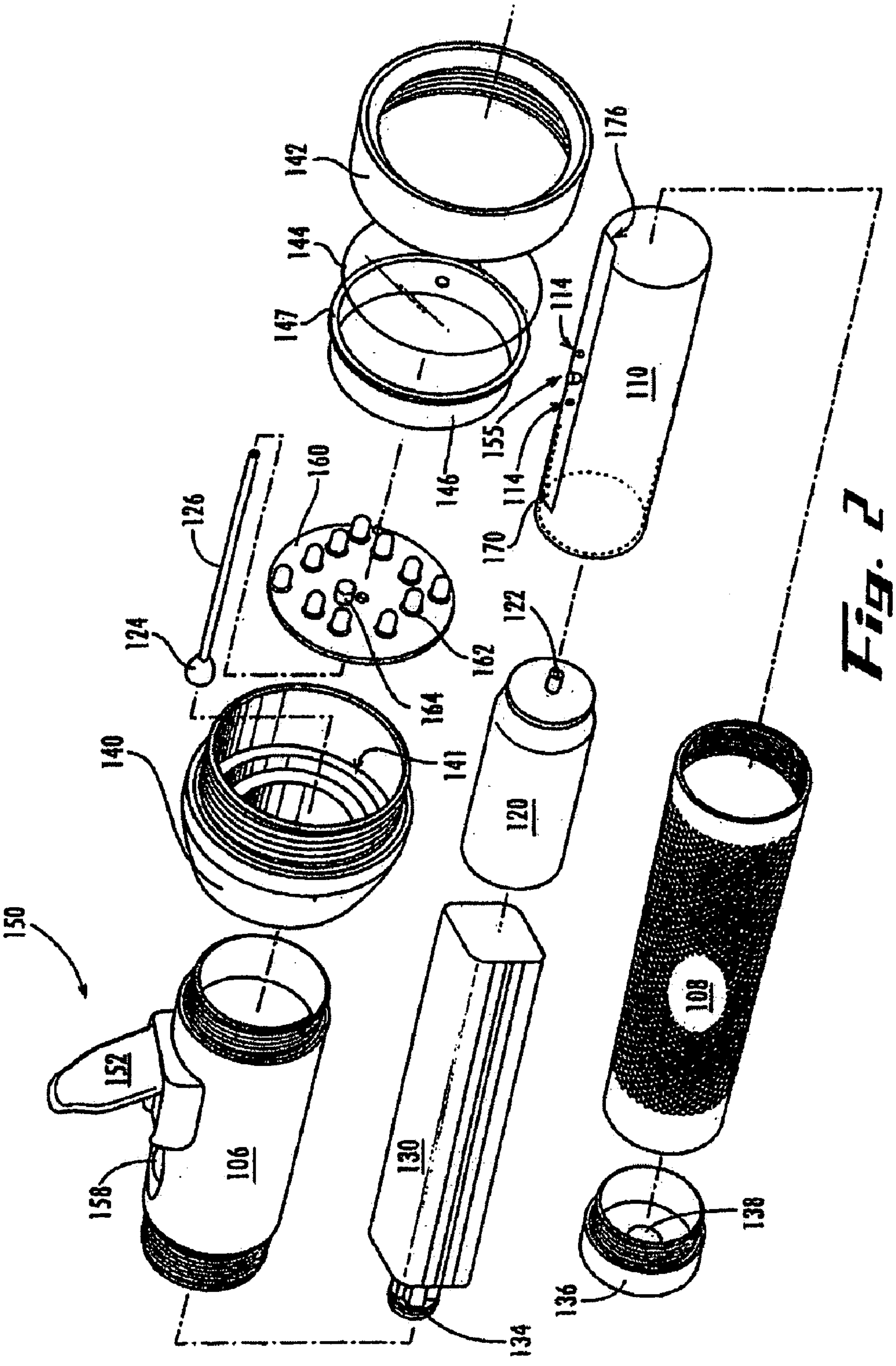
FIG. 2 is an exploded, perspective view of the self-defense flashlight as shown in FIG. 1.
Figure 3:
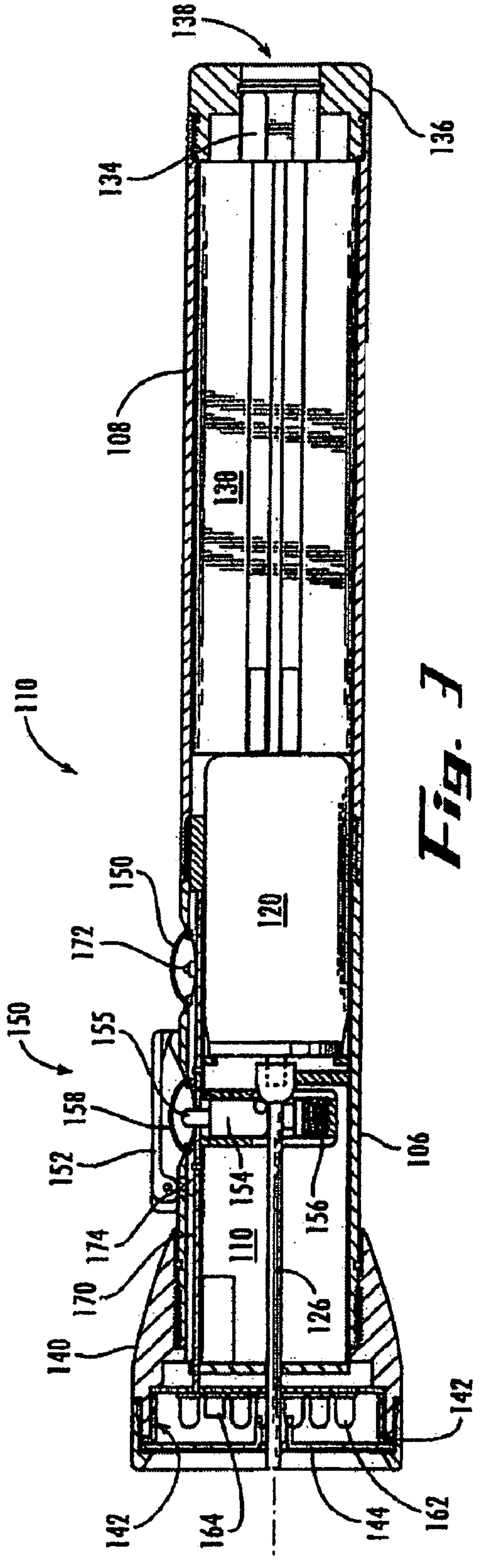
FIG. 3 illustrates a cross-sectional view of the self-defense flashlight as shown in FIG. 1.
Figure 4:
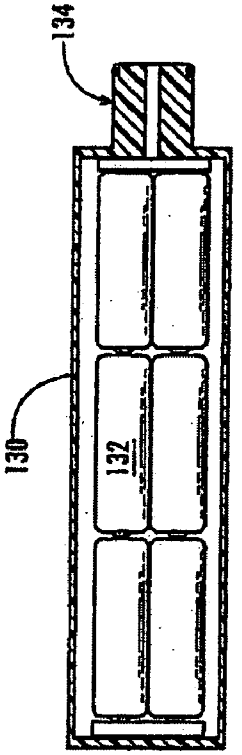
FIG. 4 illustrates a cross-sectional view of the battery housing as shown in FIG. 2.

Also located at the front end 101 of the housing 102 are the retainer 146 in the front cap 142. The retainer 146 is used to secure a first printed circuit board (PCB) 160 between a portion of the head 140 and the retainer 146 as the front cap is threadably attached to the head 140. Prior to securing the front cap 142 to the head 140, a lens 144 is placed adjacent a portion of the retainer 146 such that the lens 144 is secured in place between the front cap 142 and the retainer 146 such that the lens 144 is secured in place between the front cap 142 and the retainer 146 as the front cap is threadably attached to the head 140. The first PCB 160 preferably includes a plurality of light emitting diodes (LEDs) 162 and a laser diode 164. As well, both the first PCB 160 and lens 144 have apertures located therein such that a spray tube 126 is permitted to extend through and beyond the lens 144. This configuration allows a user to expel a substance such as teargas, pepper spray, etc., from a canister 120 (FIG. 2) located within the flashlight 100 by way of the spray tube 126. The LEDs 162 and laser diode 164 receive power by way of a light circuit (not shown) located on the first PCB 160. Preferably, the laser diode 164 provides a visible laser that allows a user to aim the flashlight 100, and subsequently the discharge of the expelled substance from the canister 120 in the desired direction. Opening the switch door 152 of the switch assembly 150 allows the user to both energize the laser diode 164 and access the switch required to emit the substance held in the internal canister 120.

Referring now to FIGS. 2–5, a preferred embodiment of the flashlight 100 further includes a canister housing 110, a canister 120, a battery housing 130, a second printed circuit board 170, and the remaining components of the switch assembly 150. One embodiment of the flashlight 100, among others, includes a battery housing 130 enclosing a plurality of batteries 132, the batteries 132 being rechargeable by way of a charging port 134 at the base of the battery housing 130. Preferably, the battery housing 130 is slidably received within the rear housing 108 of the flashlight 110 such that the charging port 134 is accessible through a chargeable aperture 138 formed in the rear cap 136. As such, the batteries 132 may be charged by way of the charging port 134 without having to remove the battery housing 130 from the flashlight 110. However, rapid replenishment of the power source may be accomplished by removing the rear cap 136 from the rear housing 108, replacing the battery housing 130 containing the spent batteries 132 with a spare battery housing 130 with charged batteries 132, and threadably reattaching the rear cap 136 to the rear housing 108. Preferably, preferred embodiments will be rechargeable from either 12 volt DC or 110 volt AC sources. Note also, embodiments are envisioned wherein a battery housing 130 is not required for containing the batteries 132, as well as embodiments wherein non-rechargeable batteries are used.

Figure 5:
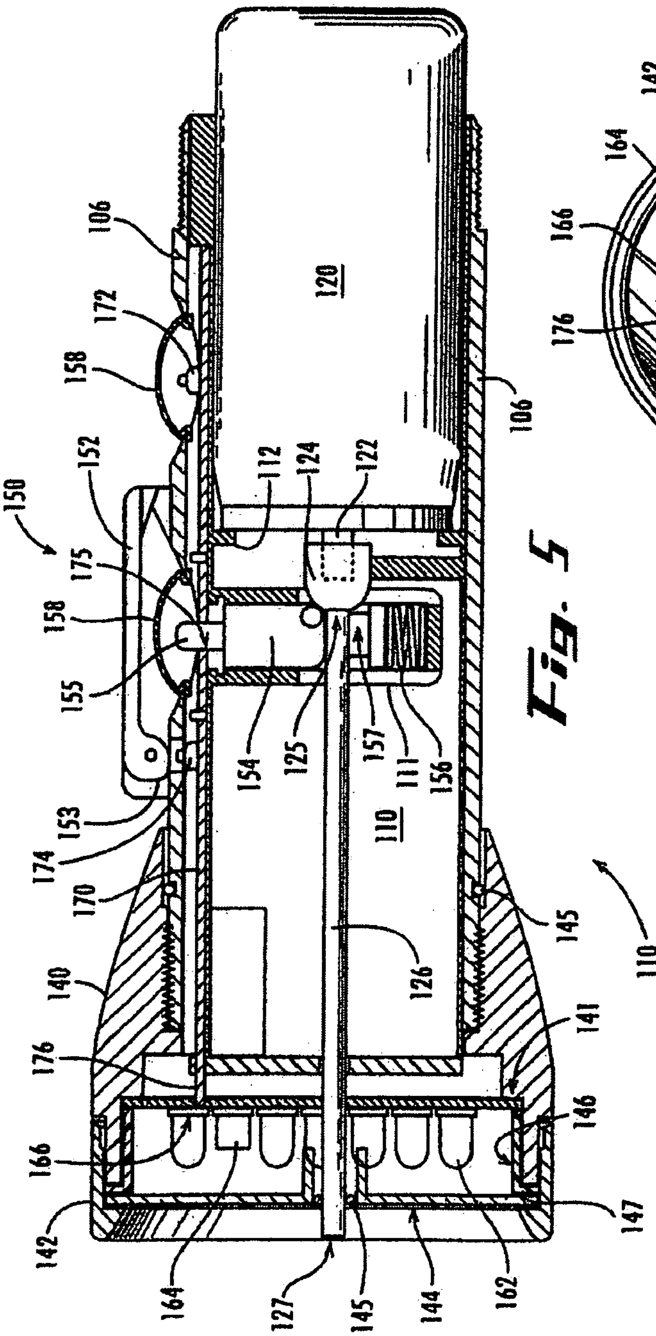
FIG. 5 illustrates a partial, cross-sectional view of the self-defense flashlight as shown in FIG. 1.
Figure 6:
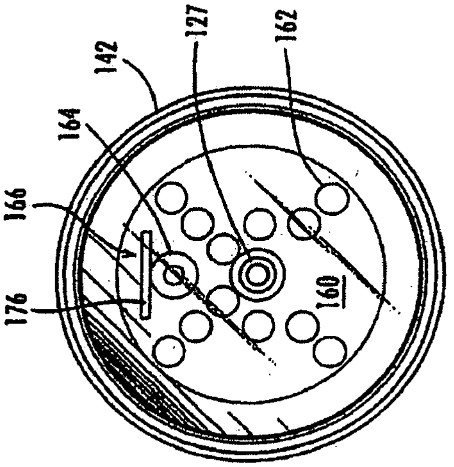
FIG. 6 illustrates a front view of the self-defense flashlight as shown in FIG. 1.
Figure 8:
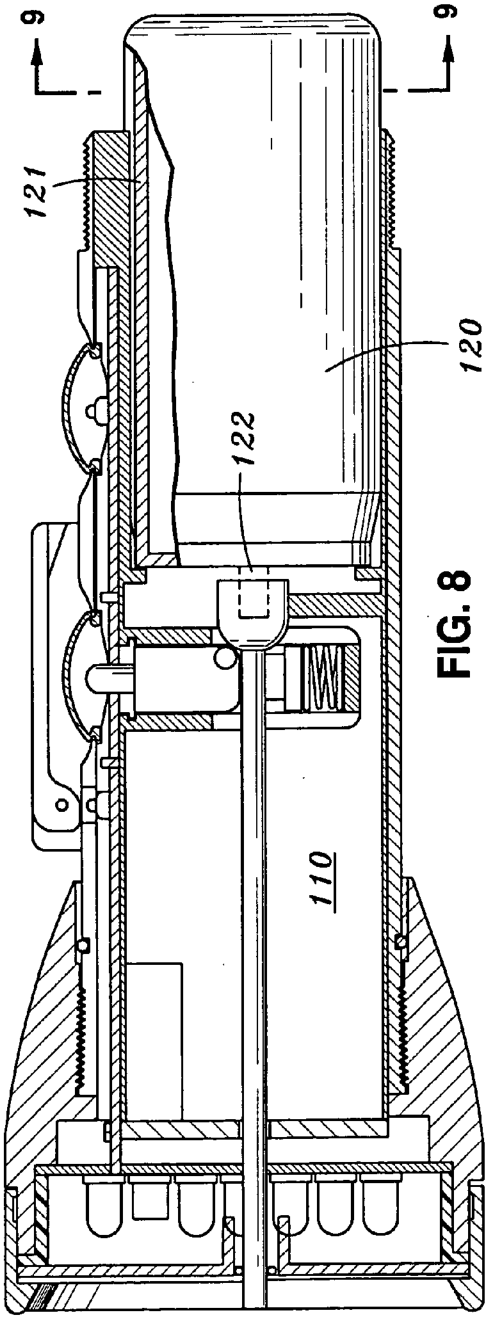
FIG. 8 is a cross-sectional view taken along line 8—8 of FIG. 7
Figure 9:
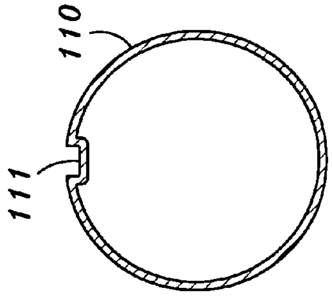
FIG. 9 is a cross-sectional view taken along 9—9 of FIG. 8.
Figure 7:
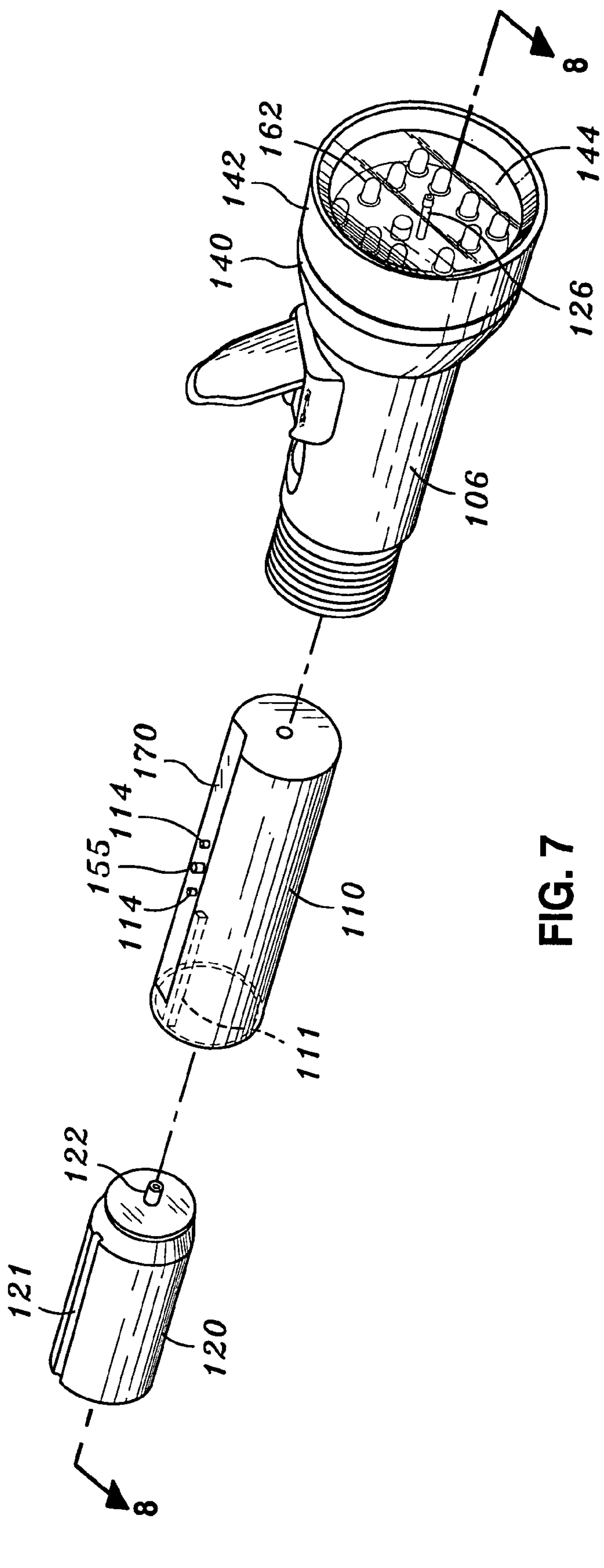
FIG. 7 is a perspective exploded view of the front housing with retainer, cap, lens, LEDs and spray tube of the flashlight of the present invention in combination with a canister housing and aerosol canister, the canister housing and aerosol canister being constructed in accordance with a preferred embodiment of the present invention.

As best seen in FIG. 5, the canister 120 is received within the canister housing 110, which is in turn slidably received within the front housing 106. In a preferred embodiment depicted in FIGS. 7–9, the canister 120 will preferably be configured to be received within the canister housing 110 such that the canister 120 is retained within the canister housing 110 in a fixed, non-rotational orientation. As shown in FIG. 7, to accomplish that end canister 120 may preferably be provided with an elongate slot or groove 121 formed along the length of such canister 120. The canister housing 110 will, in turn, be provided with an elongate projection 111 that cooperates to fit within the groove or slot 121 formed upon aerosol canister 120. As depicted in FIG. 8, the groove 121 formed upon the aerosol canister 120 will thus cause the canister to remain in a fixed, axial position while disposed within canister housing 110. In this respect, and as depicted in the cross-sectional view of FIG. 9, projection or member 111 formed upon the canister housing 110 will provide a complimentary fit to the slot or groove 121 to thus make rotational movement of the aerosol canister 120 within canister housing 110 impossible.

As will be appreciated by those skilled in the art, by providing for such precise interconnection between the aerosol canister 120 and canister housing 110, axial placement of the aerosol canister 120 may be selectively controlled such that only those aerosol canisters 120 having the precise dimensions and capabilities to interlock with canister housing 110 can be utilized in the practice of the present invention. Along these lines, it is expressly contemplated that such selective interconnection between aerosol canister 120 and canister housing 110, via the interconnection between elements 111 and 121, can be utilized to selectively control the specific types of aerosol containers that can be utilized in connection with the flashlights of the present invention. For example, the interconnection between aerosol canister 120 and canister housing 110 may be designed such that only particular brands of aerosol canisters 120 can be utilized with certain flashlight embodiments. Likewise, the interconnection between canister housing 110 and aerosol canister 120, via the interconnection of elements 111 and 121, can be configured such that only certain types of aerosol canisters 120 having a specific aerosol component therein can be utilized. With respect to the latter, it is contemplated that by selectively controlling the interconnection between aerosol canisters 120 and canister housing 110, aerosol canisters may be configured such that aerosol canisters 120 having a less-toxic aerosol component, as may be desired for flashlights of the present invention intended to be sold to the general purchasing public, be utilized, or else configured such that more toxic aerosol-containing aerosol canisters be utilized only in connection with those flashlights of the present invention intended to be sold for use in law enforcement and/or military applications.

Figure 10:
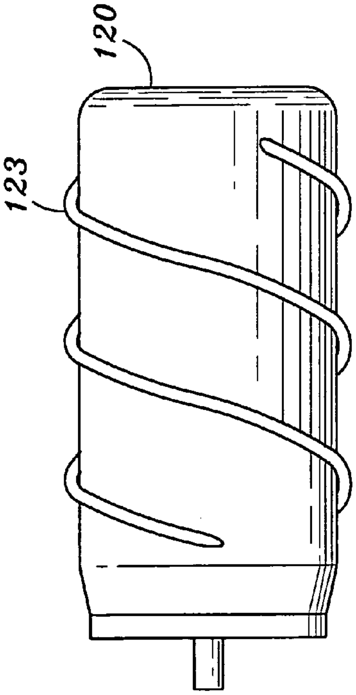
FIG. 10 is a side perspective view of an aerosol canister constructed in accordance with a preferred embodiment of the present invention.

Referring now to FIG. 10, there is shown an alternative embodiment of an aerosol canister 120 for use in the practice of the present invention. As illustrated, the aerosol canister 120 is provided with a helical projection 123 that is designed and configured to mate with a complimentary helical groove formed within canister housing 110 (not shown). As will be readily appreciated by those skilled in the art, by twisting aerosol canister 120 such that helical projection 123 mates with complimentary helical groove formed within canister housing 110, the aerosol canister 120 may thus be screwed or twisted into position within the canister housing 110.

As will be readily appreciated by those skilled in the art, the embodiments depicted in FIGS. 7–10 are only representative of a wide variety of mechanisms by which an aerosol canister 120 may be caused to selectively interlock or interconnect with canister housing 110. Accordingly, any of a variety of mechanisms by which aerosol canister 120 may be caused to selectively interconnect with canister housing 110 such that only a specific type of canister 120 can remain axially disposed in fixed position within canister housing 110 should be considered to fall within the scope of the present invention. For example, it is contemplated that any combination of grooves, apertures or detents that can form a complimentary fit with a corresponding ridge, member or projection, as will be readily understood by those skilled in the art, should be deemed to fall within the scope of the present invention.

In all such applications, it is contemplated that canister 120, which may be a standard type aerosol canister, will include a nozzle 122 that when displaced from its at rest position causes the substance contained within the canister 120 to be discharged. A spray tube mount 124 is secured to the nozzle 122, and the proximal end 125 of the spray tube 126 is secured in the spray tube mount 124. The canister 120 and attached spray tube is slidably inserted into the canister housing 110 until the front portion of the canister 120 comes into contact with the ledge 112 extending inwardly from the inner surface of the canister housing 110. By so positioning the canister 120, a user insures that the distal end 127 of the spray tube 126 passes through both the first PCB 160 in the lens 144. As well, in the preferred embodiment shown, inserting the canister 120 in this manner insures that the spray tube 126 extends through the plunger housing 111 portion of the canister housing 110 and under a portion of the plunge 154 which a user can cause to come into contact with the proximal end 125 of the spray tube 126 and/or the spray tube mount 124, as is discussed in greater detail hereinafter.

Preferably, a second printed circuit board (PCB) 170 is secured to the upper portion of the canister housing 110. A pair of projections 114 on the upper portion of the canister housing 110 mate with matching apertures on the second PCB 170 to insure proper alignment. The second PCB 170 preferably includes a light switch 172, a laser switch 174, a button aperture 175, and a plug 176. The button aperture 175 allows the button 155 of the plunger 154 to pass through the second PCB 170 so as to be accessible by a user. The plug 176 is configured to mate with a socket 166 formed in the first PCB 160, thereby connecting the circuits on the first and second PCBs 160, 170.

Preferably, a switch assembly 150 includes a switch door 152 having a camming surface 153, a plunger 154 including a button 155, and a spring 156. To prevent inadvertent discharge of substances from the canister 120, the switch door 152 is provided and is normally maintained in a closed position, thereby preventing the inadvertent depression of the plunge 154 and subsequent discharge of substance from the canister 120. The switch door 152 includes a camming surface 153 that is configured to contact laser switch 174 as the switch door 152 is moved from the closed to the open position. Contact of the camming surface 153 with the laser switch 174 provides power to the laser diode 164, which in turn emits a visible laser for aiming the flashlight 110. Similarly, when a user contacts a light switch 172, power is provided to the LEDs 162 on the first PCB 160, thereby causing illumination as desired. After a user has placed the switch door 152 in the open position, the user now has access to the button 155 which is used to urge the plunger 154 inwardly so as to contact the proximal end 125 of the spray tube 126 and/or the spray tube mount 124. Preferably, the plunger has a central portion 157 which allows the spray tube to pass through the plunger 154 in an uninhibited manner, unless the plunger 154 is being urged inwardly by a user. As well, a spring 156 is placed between a plunger housing 111 and the bottom of the plunger 154 such that the plunge 154 is urged outwardly when no pressure is being exerted on the button 155 by a user.

Operation of the flashlight 110 for use as a source of illumination merely requires a user to operate the light switch 172. The user merely presses down on the flexible boot 158, thereby eventually exerting pressure on the light switch. Activation of the light switch 172 provides power to the LEDs 162, causing them to illuminate. To secure power to the LEDs 162, the user merely depresses the light switch 172 again.

As previously noted, discharging substances from the canister 120 preferably requires that a protective switch door 152 be moved from a closed to an open position, thereby giving the user access to the plunger 154. As the switch door 152 is moved to the open position, the camming surface 153 contacts the laser switch 174, thereby causing the laser diode 164 to emit a visible laser. The visible laser can be used for aiming the flashlight 110, as well as a psychological deterrent to a would-be assailant. To discharge the substances contained in the canister 120, the user exerts pressure on the flexible boot 158, and in turn on the button 155 of the plunger 154. As the plunger 154 is urged inwardly, a portion of the plunger eventually comes into contact with a surface on the spray tube mount 124, thereby causing the spray tube mount 124 to move rearwardly and exerting force on the nozzle 122.

Eventually, enough force is exerted on the nozzle 122, thereby causing the release of the substance within the canister 120. The substance is then discharged through the spray tube 126 which lies along the central longitudinal axis of the flashlight 100, and out the distal end 127 of the spray tube 126. Note, the use of LEDs 162 rather than an incandescent bulb type configuration for illumination allows the configuration wherein the spray tube 126 lies approximately along the central longitudinal axis of the flashlight 100. After a desired amount of substance has been discharged from the canister 120, a user merely ceases to exert pressure on the button 155 of the plunge 154, thereby allowing the spring 156 to urge the plunger 154 outwardly and away from the spray tube mount 124. As pressure is released from the spray tube mount 124, the nozzle 122 returns to its at rest position, thereby causing discharge of the substance to cease.

It should be emphasized that the above-described embodiments of the present self-defense flashlight, particularly, any "preferred" embodiments, are merely possible examples of implementations, merely set forth for a clear understanding of the principles of the self-defense flashlight. Many variations and modifications may be made to the above-described embodiment(s) of the self-defense flashlight without departing substantially from the spirit and principles of the self-defense flashlight. All such modifications and variations are intended to be included herein within the scope of this disclosure of the self-defense flashlight and protected by the following claims.

What is claimed is:

1. A flashlight for dispensing a substance from an aerosol canister, the flashlight comprising:

an elongated housing having a front end, a rear end, and a central longitudinal axis;

a canister housing fixedly received within the elongated housing;

an aerosol canister slidably received by, and in a cooperatively securing notch and groove relationship with, the canister housing, whereby significant rotational movement of the aerosol canister is prevented;

wherein the cooperatively securing notch and groove relationship is formed by a projection extending inwardly from an inner surface of the canister housing and a mating groove on the aerosol canister configured to receive the projection as the, aerosol canister is slidably disposed within the canister housing;

at least one light emitting diode disposed approximate the front end of the housing; and an elongated spray tube having a proximal end and a distal end, the proximal end being connected to the aerosol canister and the spray tube extending parallel to the central longitudinal axis such that the distal end extends beyond the front end of the elongated housing.

2. A flashlight for dispensing a substance from an aerosol canister, the flashlight comprising:

an elongate housing having a front end and a rear end, the aerosol canister being slidably received in fixed position within the housing;

a means for aligningly locking the aerosol canister to the elongate housing;

a light source disposed approximate the front end of the housing;

a spray tube having a proximal end and a distal end, the proximal end being in fluid communication with the aerosol canister and the distal end extending beyond the front end of the housing; and a switch assembly including:

a plunger extending into the housing, the plunger being arranged and configured to cause the substance in the aerosol canister to be emitted through the spray tube when the plunger is urged inwardly;

a switch door operable between an open and a closed position; and wherein moving the switch door from the closed position to the open position allows a user to access the plunger.

3. The flashlight of claim 2, wherein the means for aligningly locking the aerosol canister to the elongate housing includes a canister housing, the canister housing including means for axially aligning the aerosol canister disposed on an inner surface of the canister housing, the canister housing being configured to axially receive the aerosol canister; and wherein the aerosol canister includes a mating means for aligning the aerosol canister configured to receive the means for aligning as the aerosol canister is slidably disposed in the aerosol housing.

4. A flashlight for dispensing a substance from an aerosol canister, the flashlight comprising:

an elongated housing having a front end, a rear end, and a central longitudinal axis;

a canister housing fixedly received within the elongated housing;

an aerosol canister slidably received by, and in a cooperatively securing notch and groove relationship with, the canister housing, whereby significant rotational movement of the aerosol canister is prevented;

wherein the cooperatively securing notch and groove relationship is formed by a groove formed upon an inner surface of the canister housing and a mating projection on the aerosol canister extending outwardly therefrom, the projection being configured to receive the groove as the aerosol canister is slidably disposed within the canister housing;

at least one light emitting diode disposed approximate the front end of the housing; and an elongated spray tube having a proximal end and a distal end, the proximal end being connected to the aerosol canister and the spray tube extending parallel to the central longitudinal axis such that the distal end extends beyond the front end of the elongated housing.

5. A flashlight for dispensing a substance from an aerosol canister, the flashlight comprising:

an elongate housing having a front end and a rear end, the aerosol canister being fixedly received and in a cooperatively engaging notch and groove configuration within the housing;

wherein the housing further includes a groove formed upon an inner surface of the housing and wherein the aerosol canister further includes a projection formed upon the external surface thereof, said projection being configured to be received within the groove formed upon the inner surface of the housing as the aerosol canister is fixedly disposed in the housing;

a light source disposed adjacent the front end of the housing; and a spray tube having a proximal end and a distal end, the proximal end being connected to the aerosol canister and the distal end extending beyond the front end of the housing such that the substance can be discharged therefrom in a desired direction; and a laser diode disposed approximate the front end of the housing, the laser diode being arranged to emit a laser in the desired direction of discharge.

6. The flashlight of claim 5 wherein said groove formed upon the inner surface of the housing comprising a generally helical groove and said projection comprises a generally helical projection formed radially about said aerosol canister.

* * * * *